US005104789A

United States Patent [19]

Permar et al.

[11] Patent Number: 5,104,789
[45] Date of Patent: Apr. 14, 1992

[54] MONOCLONAL ANTIBODIES WHICH DISCRIMINATE BETWEEN STRAINS OF CITRUS TRISTEZA VIRUS

[75] Inventors: Thomas A. Permar, Altamonte Springs; Stephen M. Garnsey, Winter Park, both of Fla.

[73] Assignee: The United States of America, as represented by the Secretary of Agriculture, Washington, D.C.

[21] Appl. No.: 351,347

[22] Filed: May 15, 1989

[51] Int. Cl.$^5$ .............................................. C12Q 1/70

[52] U.S. Cl. ........................................ 435/5; 435/7.1; 435/70.21; 435/240.27; 530/388.3

[58] Field of Search .................... 530/387; 435/5, 7.1, 435/70.21, 240.27

[56] References Cited

PUBLICATIONS

Gumpf et al.: Production & Evaluation of Specific Monoclonal Antibodies to Citrus Tristenza Virus Strains, Phytophylactica, vol. 19 (2), 1987 pp. 159-162.

C. Vela et al., "Production and Characterization of Monoclonal Antibodies Specific for Citrus Tristeza Virus and Their Use for Diagnosis," J. Gen. Virol. 67: 91-96 (1986).

S. M. Garnsey et al., "Serological Titer of Citrus Tristeza Virus (CTV) Isolates of Varying Severity in Different Citrus Hosts," Phytopathology 75: 1311 (Abstract) (1985).

D. J. Gumpf et al., "Production and Evaluation of Specific Monoclonal Antibodies to Citrus Tristeza Virus Strains," Phytophylactica 19(2): i, 159-161 (Jun. 1987) (complete copy).

*Primary Examiner*—Christine Nucker
*Assistant Examiner*—Jeffrey Stucker
*Attorney, Agent, or Firm*—M. Howard Silverstein; Curtis P. Ribando; Curtis P. Ribando

[57] ABSTRACT

Monoclonal cell lines producing antibodies to severe citrus tristeza virus have been developed. The antibodies react with crude plant extracts infected with severe isolates, but not with crude plant extracts infected with mild isolaates or healthy plant tissue. This immunological probe has been utilized in enzyme-linked immunosorbent assays as a rapid technique for identifying citrus infected with severe isolates of CTV. Field tests on recently planted trees in a commercial citrus grove have verified the effectiveness of the immunoassay.

10 Claims, No Drawings

MONOCLONAL ANTIBODIES WHICH DISCRIMINATE BETWEEN STRAINS OF CITRUS TRISTEZA VIRUS

BACKGROUND OF THE INVENTION

1. Field of the Invention

This invention relates to murine hybridoma cell lines and monoclonal antibodies produced therefrom which may be used to detect severe forms of the citrus tristeza virus in citrus plant tissue by immunological assay.

2. Description of the Prior Art

A foreign entity such as a virus can be used to provoke an immune response in a mouse. Antibody-producing white blood cells of the mouse react to many specific sites on the virus, called antigenic determinants. By selecting a white blood cell that produces antibody to an antigenic determinant present only on one type or class of virus, a researcher is able to develop an immunological probe which can identify that type of virus without reacting to all other viruses. The antibody-producing cell is fused with a cancer cell (myeloma), resulting in a new cell that retains the properties of both parent cells. The new cell (hybridoma) still produces the desired antibody, but now is immortal like the cancer cell. In practical terms, this means that the hybridoma is a constant and unlimited source of a single type of antibody that never varies qualitatively. Hybridomas that have been selectively cloned several times are called monoclonal antibodies [Goding, "Monoclonal Antibodies: Principles and Practice," pp. 5-40, Academic Press Inc., London (1983)].

Citrus tristeza virus (CTV) is the cause of severe stem pitting and decline diseases of citrus and is one of the most economically important citrus pathogens worldwide [Bar-Joseph et al., Proc. Intern. Soc. Citriculture 1: 419-422 (1981); Whiteside et al. (eds.), "Compendium of Citrus Diseases," pp. 48-50, APS Press, St. Paul, Minn. (1988)]. There is great diversity of symptoms induced among different isolates of CTV, and symptom severity is often host specific [Garnsey et al., Phytophylactica 19: 151-157 (1987)]. Currently, severity of a given isolate can only be determined by inoculating differential indicator plants or the commercial host [Garnsey et al., supra (1987)]. This is time consuming and not satisfactory for many applications.

Serological tests for CTV have been developed [Brlansky et al., Proc. 9th Conf. Intern. Organ. Citrus Virol., Garnsey et al. (eds.), pp. 337-342, IOCV, Gainesville, Fla. (1984); Garnsey et al., Phytopathology 68: 88-95 (1979)], and enzyme-linked immunosorbent assay (ELISA) tests have been widely used for survey, certification, and eradication work as well as for research [Cambra et al., Proc. Intern. Soc. Citriculture 1: 444-448 (1982); Garnsey et al., Proc. Intern. Soc. Citriculture 1: 448-452 (1981); Ke et al., Proc. 9th Conf. Intern. Organ. Citrus Virol., Garnsey et al. (eds.), pp. 70-75, IOCV, Riverside, Calif. (1984)]. Polyclonal antisera have been made to different isolates in several animal species [Garnsey et al., supra (1981)], and a monoclonal antibody also has been produced and made available commercially [Vela et al., J. Gen. Virol. 67: 91-96 (1986)]. The polyclonal and monoclonal antibodies reported are all reactive to a wide range of CTV isolates of differing severity [Garnsey et al., Phytopathology 75: 1311 Abstract (1985); Vela et al., supra (1986)]. These immunological probes are useful for general detection of CTV infection, but do not provide information about biological severity.

The lack of evidence for serological diversity among CTV isolates is consistent with analysis of peptide digests of different isolates which also indicated only small differences in coat protein chemistry among the isolates evaluated [Lee and Calvert, Phytophylactica 19: 205-210 (1987)]. Other approaches, such as cDNA probes [Rosner et al., Phytopathology 76: 820-824 (1986)] and dsRNA analysis [Dodds et al., Phytophylactica 19: 131-137 (1987)], so far lack the desired specificity or reliability, or are not adaptable for rapid, large-scale assays. There is a need for a rapid diagnostic procedure to identify specific severe isolates of CTV. Brlansky et al. [supra] and Vela et al. [Proc. 10th Conf. Intern. Organ. Citrus Virol., Timer et al. (eds.), pp. 55-61, IOCV, Riverside, Calif. (1988)] have suggested that multiple epitopes exist in the CTV coat protein based, respectively, on results obtained with different polyclonal antisera and with different monoclonal antibodies. Vela et al. [supra (1988)] also suggested these epitopes were common to all CTV isolates tested. However, evidence that some epitopes may be strain specific was obtained with polyclonal antiserum to T-36 that showed greater avidity to homologous antigens than to heterologous antigens, whereas antiserum to CTV isolate T-4 reacted equally with both antigens.

SUMMARY OF THE INVENTION

We have discovered that CTV-MCA13, a monoclonal antibody produced to the Florida citrus tristeza virus (CTV) isolate T-36, reacts to decline-inducing, seedling yellows, and stem pitting isolates of CTV from Florida, California, and Spain. It does not react to mild CTV isolates from these same areas which produce symptoms only in Mexican lime. All CTV antigen sources used reacted strongly to polyclonal antibodies in double sandwich ELISA and to a CTV polyspecific Spanish monoclonal (3DF1) in comparable double antibody sandwich indirect ELISA assays. Discrimination of CTV isolates was similar in indirect ELISA tests with plate-trapped antigen and in double antibody sandwich indirect ELISA tests with antigen trapped on polyclonal antibody-coated plates. The monoclonal is an IgG2a immunoglobulin and did not react to extracts of healthy citrus or citrus infected with other viruses.

It is an object of this invention to provide murine hybridoma cell lines which produce monoclonal antibodies specific to severe CTV isolates and do not react to mild CTV isolates.

It is a further object of this invention to provide monoclonal antibodies as immunochemical reagents for the diagnosis of severe CTV infections.

Other objects and advantages of the invention will become readily apparent from the ensuing description.

DETAILED DESCRIPTION OF THE INVENTION

We have now constructed murine hybridoma cell lines which produce monoclonal antibodies that react selectively with severe CTV and do not react to mild CTV isolates.

Hybridoma cell line designated CTV-MCA13 has been deposited under the conditions of the Budapest Treaty with the American Type Culture Collection, Rockville, Md., and has been assigned the number ATCC HB-10140.

All monoclonal antibodies which bind selectively to severe CTV are encompassed by this invention.

These antibodies will permit the quick and accurate diagnosis of severe CTV infections and greatly enhance cross protection research efforts [see Fulton, Ann. Rev. Phytopath. 24: 67-81 (1986)].

The monoclonal antibodies are produced by hybrid cells which are constructed using conventional techniques [see Kohler and Milstein, Nature 256: 495-497 (1975)].

The antibodies are of the IgG2a type and bind selectively to severe CTV.

As is well known in the field of monoclonal antibodies, each independent cell line which produces a monoclonal antibody specific for the same antigen is nonetheless different from all others, as is each of the monoclonal antibodies so produced.

While repetition of the procedures described herein will result in production of hybrid cell lines which produce monoclonal antibodies specific for severe CTV, it is unlikely that it will yield cell lines which produce monoclonal antibodies that are chemically exact copies of the monoclonal antibody described herein.

CTV viral isolates were originally obtained from infected citrus trees in Florida. These isolates were maintained on citrus stock and varied in the symptoms produced in the citrus plants; T-36 was severe, T-4 and T-26 were mild. Isolate T-36 was used to produce the antibody described herein. Viral purification was accomplished using the technique of Lee et al., Phytopathology 77: 543 (1987). The T-36 strain of CTV is continuously maintained and available from the following sources:

---

Dr. R. F. Lee
University of Florida
IFAS-CREC
700 Experiment Station Road.
Lake Alfred, FL 33850

Dr. C. L. Nibleck
Plant Pathology Department
University of Florida-IFAS
Gainesville, FL 32611

Dr. E. L. Civerolo
USDA-ARS-HSI
Fruit Laboratory
Beltsville, MD 20705

Dr. S. M. Garnsey or
Dr. R. K. Yokomi
USDA-ARS-SAA
Horticultural Research Laboratory
2120 Camden Road
Orlando, FL 32803

---

Balb/c mice were immunized by intraperitoneal (IP) injection with purified T-36 CTV in Freund's complete adjuvant. These mice were hyperimmunized by intravenous injection at one and ten months after the initial immunization. Three days after the final injection, spleen cells were harvested and fused with Sp2/0 Ag-14 myeloma cells using the technique of Van Deusen and Whetstone [Proc. 24th Annu. Meeting Amer. Assoc. Vet. Lab. Diagnosticians 24: 211-228 (1981)]. Blood removed from the hyperimmunized mouse by cardiac puncture was saved as a positive control.

Two weeks after plating, primary hybridomas were screened by indirect ELISA using plate-trapped antigens. Selected positive hybridomas were cloned three times by limiting dilution. Specific antibody was produced by injecting pristine primed mice with approximately $10^6$ cloned cells IP. The resulting ascites fluid was centrifuged and filtered. Aliquots were either frozen or purified by affinity chromatography.

The fusion of spleen and myeloma cells yielded 960 wells with actively growing primary hybridoma colonies. Media was taken from each well for testing against healthy plant tissue and plant tissue infected with CTV isolate T-36. This screening assay showed 140 wells with primary hybridomas which produced antibodies that reacted with T-36 infected tissue but did not react with health plant tissue.

These 140 primary hybridomas were retested with T-36 infected and healthy tissue extracts, as well as tissue extracts containing CTV isolates T-4 and T-26.

Primary hybridomas in the second screening assay were separated into five groups. Those that reacted: (1) only to T-36 infected tissue; (2) with all CTV infected tissue in the test; (3) to T-36 and T-26 infected tissue more than to T-4 infected tissue; (4) to T-36 and T-4 infected tissue more than to T-26 infected tissue; and (5) to T-26 infected tissue to a greater extent than to T-36 and T-4 infected plant tissue.

The specificity of one of the 25 cell lines from Group 1 which reacted only to T-36 is further described here. We have designated this cell line as CTV-MCA13, ATCC No. HB10140. This cell line was cloned twice, and ascites fluid was produced containing antibody of the IgG2a immunoglobulin class and subclass.

Extracts were assayed from citrus plants infected with 13 different CTV isolates selected to represent a wide range of biological severity and three different geographic areas. Dilution factors calculated for each extract source to yield an approximately uniform reaction in the polyclonal DAS reference test ranged from 1/40 to 1/800 (Table I). These extracts were tested in a double sandwich indirect assay against CTV-MCA13 and against the CTV polyspecific monoclonal 3DF1 [Vela et al., supra (1988)]. All 13 extracts reacted positively to 3DF1 and all but two $A_{405}$ values ranged from 0.86 to 1.16 (Table I). In contrast, only 6 of the 13 extracts reacted to the CTV-MCA13 antibody (Table I) with $A_{405}$ values from 0.34 to 0.87. These six isolates all have been associated with decline in sweet orange grafted on sour orange, seedling yellows, and/or stem pitting in sweet orange or grapefruit (Table II). The isolates which did not react to CTV-MCA13 cause symptoms in Mexican lime of varying severity, but do not cause decline, seedling yellows, or stem pitting symptoms in grapefruit and sweet orange.

TABLE I

Reactivity of CTV-MCA13 and the Commercially Available 3DF1 Monoclonal Antibodies to 13 CTV Isolates and 3 Nonrelated Viruses and a Viroid in Double Antibody Sandwich and Plate-Trapped Antigen ELISA

| Antigen | | | Indirect ELISA Reaction ($A_{405}$ Mean ± SD) | | | |
|---|---|---|---|---|---|---|
| | | | Double Antibody Sandwich | | Plate-Trapped Antigen | |
| Designation | Source[a] | Extr. Dilut. | CTV-MCA13 | 3DF1 | CTV-MCA13 | 3DF1 |
| Healthy | Fl | 1/50 | 0.06 ± 0.02 | 0.05 ± 0.01 | 0.01 ± 0.01 | 0.02 ± 0.05 |
| T-4 | Fl | 1/80 | 0.06 ± 0.00 | 1.03 ± 0.04 | 0.06 ± 0.04 | 0.74 ± 0.04 |
| T-26 | Fl | 1/80 | 0.05 ± 0.00 | 0.93 ± 0.03 | 0.03 ± 0.02 | 0.42 ± 0.06 |
| T-30 | Fl | 1/50 | 0.06 ± 0.00 | 0.96 ± 0.06 | 0.07 ± 0.07 | 0.59 ± 0.06 |
| T-36 | Fl | 1/50 | 0.78 ± 0.06 | 1.01 ± 0.02 | 0.58 ± 0.06 | 0.57 ± 0.09 |
| T-66a | Fl | 1/200 | 0.87 ± 0.10 | 1.04 ± 0.01 | 1.03 ± 0.13 | 0.70 ± 0.08 |
| T-68 | Fl | 1/80 | 0.60 ± 0.03 | 1.02 ± 0.03 | 0.52 ± 0.06 | 0.52 ± 0.08 |
| T-514 | Ca | 1/300 | 0.09 ± 0.00 | 0.54 ± 0.01 | 0.06 ± 0.02 | 0.47 ± 0.09 |
| T-516 | Ca | 1/300 | 0.11 ± 0.00 | 0.86 ± 0.02 | 0.04 ± 0.02 | 0.68 ± 0.12 |
| SY-568 | Ca | 1/80 | 0.79 ± 0.04 | 1.16 ± 0.03 | 1.12 ± 0.17 | 0.94 ± 0.14 |
| SY-576 | Ca | 1/800 | 0.34 ± 0.00 | 0.53 ± 0.01 | 0.95 ± 0.12 | 0.86 ± 0.17 |
| T-300 | Sp | 1/40 | 0.07 ± 0.01 | 1.05 ± 0.03 | 0.06 ± 0.04 | 0.42 ± 0.06 |
| T-385 | Sp | 1/40 | 0.07 ± 0.01 | 1.08 ± 0.04 | 0.04 ± 0.02 | 0.43 ± 0.08 |
| T-388 | Sp | 1/100 | 0.47 ± 0.01 | 0.90 ± 0.04 | 0.46 ± 0.09 | 0.37 ± 0.03 |
| CLRV-2[b] | Fl | 1/20 | | | 0.05 ± 0.02 | |
| CVV-2[c] | Fl | 1/20 | | | 0.00 ± 0.02 | |
| E-16B[d] | Fl | 1/20 | | | 0.00 ± 0.05 | |
| TL-CSV-4[e] | Fl | 1/20 | | | 0.06 ± 0.03 | |

[a] Fl = Florida; Ca = California; Sp = Spain.
[b] CLRV-2 is citrus leaf rugose virus, an Ilar virus.
[c] CVV-2 is citrus variegation virus, also an Ilar virus.
[d] E16B is citrus exocortis viroid.
[e] TL-CSV-4 is citrus tatterlead-citrange stunt virus.

TABLE II

Symptom Severity of 13 Citrus Tristeza Virus Isolates in Five Citrus Indicators

| CTV Isolate | | Host Plant | | | | | Profile[b] Score | Cum.[c] Score |
|---|---|---|---|---|---|---|---|---|
| Designation | Source[a] | Mex. Lime | on Sour | Swt Sour Sdlg. | Grape-fruit | MV Swt Or. | | |
| T-4 | Fl | 2[d] | 0 | 0 | 0 | 0 | 2:0:0:0:0 | 2 |
| T-26 | Fl | 1 | 0 | 0 | 0 | 0 | 1:0:0:0:0 | 1 |
| T-30 | Fl | 1 | 0 | 0 | 0 | 0 | 1:0:0:0:0 | 1 |
| T-36 | Fl | 2 | 2 | 2 | 0.5 | 0 | 2:4:3:2:0 | 14 |
| T-66a | Fl | 2 | 2 | 0.5 | 0 | 0 | 2:4:2:0:0 | 8 |
| T-68 | Fl | 2 | 3 | 2 | 1 | 0 | 2:6:6:4:0 | 18 |
| T-514 | Ca | 2 | 0.5 | 0 | 0.5 | 0 | 2:1:0:2:0 | 3 |
| T-516 | Ca | 1 | 0.5 | 0 | 0 | 0 | 1:1:0:0:0 | 2 |
| SY-568 | Ca | 3 | 3 | 3 | 2 | 3 | 3:6:9:8:15 | 41 |
| SY-576 | Ca | 3 | 3 | 2 | 2 | 1 | 3:6:6:4:5 | 24 |
| T-300 | Sp | 2 | 0.5 | 0 | 0 | 0 | 2:1:0:0:0 | 3 |
| T-385 | Sp | 1 | 0 | 0 | 0 | 0 | 1:0:0:0:0 | 1 |
| T-388 | Sp | 3 | 3 | 2 | 2 | 1 | 3:6:6:8:5 | 28 |

[a] Fl = Florida; Ca = California; Sp = Spain.
[b] Weighted profile score determined by score of the host reaction multiplied by a weighing factor of:
1 for Mexican lime (Mex. lime)
2 for stunting in grafted combinations of sweet orange on sour orange (swt. on sour)
3 for seedling yellows (SY) in sour orange seedlings (sour sdlg.)
4 for SY and stem pitting in grapefruit seedlings (grapefruit)
5 for stem pitting and stunting in Madam Vinous sweet orange (MV swt or.)
[c] Sum of profile scores.
[d] Symptom severity rated on a scale of 0 to 3, with 3 being the most severe.

A similar discrimination of severe isolates by CTV-MCA13 antibody was observed in plate-trapped antigen (PTA) indirect ELISA tests with the same extracts (Table I). Although specificity of CTV-MCA13 was not affected by the type of ELISA assay utilized, CTV-MCA13 had a stronger reaction in the PTA indirect ELISA, relative to the 3DF1 MCA, than in the double antibody sandwich (DAS) ELISA (Table I). No reaction was observed to extracts from citrus plants infected with three citrus viruses unrelated to CTV (CVV, CLRV, and TLCSV) and with citrus exocortis viroid. The CTV-MCA13 monoclonal antibody prepared to CTV isolate T-36 reacts differentially to the mild and severe CTV isolates tested. Previous work by Vela et al. [supra (1986)] and Gumpf et al. [Phytophylactia 19: 159–161 (1987)], and the demonstration of quantitative differences in reaction between specific antibody-antigen combinations had suggested that some antigenic variability could exist among isolates of CTV. This invention, however, provides the first direct evidence for a specific epitope which occurs at diagnostic levels in some CTV isolates and is absent in others.

Immunoelectron microscopy indicated that CTV-MCA13 did not bind to whole virus particles. Serum-specific electron micrographs (SSEM) of grids coated with purified 879 antiserum showed large numbers of trapped virus particles, whereas micrographs of grids coated with CTV-MCA13 showed no trapped virus. In the immunogold labeling procedures, grids coated with polyclonal 879 anti-CTV antibody first followed by CTV-MCA13 and an antimouse gold-labeled antibody were compared to control grids without CTV-MCA13. Both showed large numbers of trapped virus particles, but gold labeling was reduced in the control grids. The gold particles appeared to be randomly scattered through the grids rather than binding to the whole virus.

The exact nature and location of the epitope is unknown at present, but the lack of gold labeling of intact virus particles in immunoelectron microscopy and the high activity of the antibody against plate-trapped antigen relative to double antibody sandwich ELISA suggests that it may be a cryptic epitope [Dore et al., Virology 162: 279-289 (1989)]. An assumption is made that virus extracts contain both whole and partially degraded virus and that the polyclonal antiserum contains antibodies which will bind to cryptic epitopes exposed on those degraded virus particles.

The CTV-MCA13 antibody reacted with its homologous isolate, T-36, and to 5 to the 12 other isolates tested (Table I). Most, if not all, of these five have biological properties distinct from T-36. All produce decline or stunting in trees grafted on sour orange rootstocks and/or stem pitting in grapefruit or sweet orange. The seven isolates which did not react to CTV-MCA 13 cause symptoms in Mexican lime but do not cause significant stunting in sweet orange grafted on sour orange under greenhouse conditions, seedling yellows, or stem pitting in grapefruit or sweet orange. Preliminary tests with a broader range of CTV isolates have confirmed this pattern.

Without desiring to be bound to any particular theory of operation, we believe that specificity of CTV-MCA 13 is correlated with a specific property of the virion coat protein of reactive isolates. Although no direct correlation to a viral gene expression factor which regulates pathogenicity has been established, results so far show that this antibody is useful for rapidly identifying isolates of CTV which cause economic injury in major citrus cultivars. CTV-MCA13 will be useful for detecting the presence of severe isolates of CTV where mild and severe isolates exist.

In Spain and California, severe isolates of CTV have been introduced from other citrus-growing regions. These isolates threaten major production areas [Ballester-Olmos et al., Proc. 10th Conf. Intern. Organ. Citrus Virol., Timmer et al. (eds.), pp. 28-32, IOCV, Riverside, Calif. (1988a); Bar-Joseph et al., supra (1981); Whiteside et al., (eds.), supra] unless they can be identified and removed before extensive secondary spread occurs. The CTV-MCA13 monoclonal can be used in screening assays to avoid propagation of trees infected with severe isolates. For example, some of the ca. 27,000 registered budwood source trees in Florida have become infected with strong, decline-inducing isolates of CTV. These trees remain symptomless since they are grafted on CTV-tolerant rootstocks, but propagation on sour orange causes severe stunting. It is not practical to index large numbers of budwood trees at frequent intervals on citrus indicator plants, but this could be readily done by ELISA with a discriminating antibody such as CTV-MCA13.

There has also been intense interest in mild strain cross protection as a control strategy for CTV [Lee et al., Phytophylactica 19: 215-218 (1987); Miyakawa, Phytophylactica 19: 193-198 (1987)]. A major obstacle has been lack of a rapid means to evaluate protective ability of mild strains. Use of a discriminating antibody such as CTV-MCA13 will greatly assist evaluation of replication and movement of the challenge isolate following inoculation. It will also allow quantitative evaluation of results.

The high activity of CTV-MCA13 in PTA indirect ELISA tests again is a favorable property for large-scale screening applications. Neither the polyclonal antisera tested nor 3DF1 show strong affinity to plate-trapped CTV antigens.

The following examples are intended only to further illustrate the invention and are not intended to limit the scope of the invention which is defined by the claims.

EXAMPLE 1

Virus Isolates

Isolates of CTV used in this study were maintained in glasshouse-grown citrus plants, usually sweet orange [Citrus sinensis (L.) Osb.] or Mexican lime [C. aurantifolia (Christm.) Swing.]. Isolates foreign to the United States were maintained in a quarantine glasshouse at Beltsville, Md. [Garnsey et al., supra (1987)]. These isolates have been used in other studies and were already characterized to some extent. Most were free of other viruses or viruslike pathogens, based on indexing tests and/or aphid transmission of the CTV to virus-free citrus seedlings prior to their use in these studies. Isolates ranged in severity from those which produced mild symptoms in Mexican lime and essentially no symptoms in other hosts to those which produced stunting or decline in grafted combinations of sweet orange on sour orange [C. aurantium (L.)], seedling yellows (SY) in sour orange seedlings, and stem pitting (SP) in grapefruit [C. paradisi Macf.] and/or sweet orange seedlings [Bar-Joseph et al., supra (1981); Garnsey et al., supra (1987)]. The severity of reaction of these isolates in a standard set of five indicators [Garnsey et al., supra (1987)] is summarized in Table II. This information was derived from comparative biological assays at Beltsville, Md. [Garnsey et al., supra (1987)] and other published reports [Ballester-Olmos et al., Proc. 10th Conf. Intern. Organ. Citrus Virol., Timmer et al. (eds.), pp. 22-27, IOCV, Riverside, Calif. (1988b); Ballester-Olmos et al., supra (1988a); Rosner, supra].

Isolates used for production of the various antisera in this study were T-4, T-36, and T388. Isolate T-36, which was used to produce the discriminating antibody described herein, causes a moderately strong reaction in Mexican lime, a moderate decline in sweet/sour trees, and moderate SY reaction in sour orange seedlings, and slight pitting in grapefruit and sweet orange [Rosner, supra]. It is transmissible by *Aphis gossypii*. The T-26 and T-4 isolates used for preliminary screening of hybridomas produce only a reaction in Mexican lime [Garnsey et al., supra (1979)].

The exocortis viroid, citrus leaf rugose, citrus variegation, and tatterleaf-citrange stunt virus sources used in tests to verify specificity were standard, well-characterized glasshouse sources free of CTV. Sources of health citrus tissue used in this study were glasshouse-grown, virus-free plants.

EXAMPLE 2

Preparation of Plant Extracts

Unless specifically noted, tissue used for antigen preparation was bark from shoots of new growth collected when virus titer was expected to be near optimum [Garnsey et al., supra (1979)]. Extracts from CTV-infected and healthy plants were used to screen hybridomas and to conduct specificity assays. Crude extracts were used for screening and evaluation because of the difficulty in preparing highly purified virus in sufficient quantity from a large number of sources. Fresh extracts were prepared by grinding coarsely chopped tissue in 0.05M Tris buffer, pH 7.8, with a dispersion homogenizer. The extracts were filtered through cheesecloth to remove debris, stored on ice, and used within 1 day of preparation. For applications requiring a consistent source of antigen, uniform freeze-dried extracts were prepared by powdering coarsely chopped tissue in liquid nitrogen with a mortar and pestle. Three volumes of cold 0.05M Tris buffer, pH 7.8, which contained 50 mg/ml sucrose was added to the ice powder, and the mixture was extracted by a dispersion homogenizer. The extract was filtered through cheesecloth, frozen on dry ice, and lyophilized in 1- or 2-ml aliquots with a freeze dryer equipped with a shelf freezer and stoppering device. Lyophilization was for 4 hr with gradually increasing shelf temperature ($-25°$ to $+6°$ C.). Freeze-dried extracts were rehydrated to the desired volume in distilled water and used the same day.

Relative concentration of viral antigens in CTV-infected plant tissue was estimated by DAS ELISA using a purified polyclonal antibody (879) and a dilution series of each antigen source. Based on the reaction curves, dilutions were determined for a retention of $A_{405}=0.8$ to 1.0. These dilution values were used in all subsequent tests.

EXAMPLE 3

Isolation and Purification of T-36 CTV

Bark and leaf tissue in 50- to 300-g lots were frozen in a large mortar on dry ice and pulverized, then transferred to another mortar at room temperature and homogenized in 0.10M Tris-Cl buffer, pH 8.4, containing 0.1% (v/v) polyethylene glycol p-isooctylphenyl ether (PGIE)(Triton X-100)(extraction buffer). The final ratio of extraction buffer to fresh weight of the tissue was 5 ml/g. The extract was centrifuged at $10,000 \times g$ for 20 min, and then polyethylene glycol (PEG, MW of 6,000) and NaCl were added to the supernatant to a final concentration of 4 and 0.8% (w/v), respectively. The suspension was stirred to 1 hr at 4° C., and the precipitate was collected by centrifuging at $10,000 \times g$ for 20 min. The pellet was resuspended in 0.04M potassium phosphate buffer, pH 8.0, at a ratio of 1.3 ml/g of tissue. The suspension was stirred for 1 hr at 4° C., and the resuspended pellet was centrifuged at $5,000 \times g$ for 10 min. The supernatant was collected, made to a final concentration of 5% PEG and 1% NaCl, and stirred for 1 hr in the cold. The mixture was centrifuged at $10,000 \times g$ for 15 min. The pellet was resuspended in 30 ml of 0.05M Tris-Cl, pH 8.0, and stirred at 4° C. for 1 hr. After centrifugation at $5,000 \times g$ for 10 min, 5 ml of the supernatant was layered on top of a cesium sulfate ($Cs_2SO_4$) preformed step isopycnic (PSI) gradient. The gradients were centrifuged overnight at 36,000 rpm at 4° C. in a Beckman SW 41 rotor.

The virus zone was collected from the PSI gradients after centrifugation and dialyzed overnight against 0.05M Tris-Cl buffer, pH 8.0, to obtain a more highly purified virus preparation. The virus preparation was centrifuged at $10,000 \times g$ for 10 min, and the supernatant was adjusted to 22 ml with 0.05M Tris-Cl buffer, pH 8.0, mixed with 17.0 ml of a 53% (w/v) solution of $Cs_2SO_4$ in 0.05M Tris-Cl buffer, pH 8.0, then sealed in a quick seal Vti50 centrifuge tube (Beckman Instrument, Palo Alto, Calif.). The tubes were centrifuged for 24 hr at 50,000 rpm at 4° C. and then fractionated.

EXAMPLE 4

Production of Monoclonal Antibodies

Balb/c mice were immunized by intraperitoneal injection (IP) with 100 µg of CTV T-36 isolate in a 1:1 mixture of complete Freund's adjuvant. The mice were hyperimmunized with 50 µg of T-36 in phosphate buffered saline (PBS) at 1 month and 10 months by intravenous injection. Spleen cells were harvested 3 days after the final immunization and fused with Sp 2/0 AG-14 myeloma cells using the technique of Van Deusen and Whetstone [supra]. Blood removed from the hyperimmunized mouse by cardiac puncture was saved as a positive control. The spleen was removed aseptically, placed in a 60-mm culture dish, and perfused with 1 ml of Dulbecco's modified Eagle's medium (DMEM). The tissue was pulped into a single-cell suspension by gently pushing the spleen through an 80-mesh collector tissue sieve. Spleen cells were added to exponentially growing Sp 2/0 cells in 1:2 mixture, followed by centrifugation at 2,000 RCF for 10 min. After removal of the supernatant, the pellet was resuspended and the cells were fused with 1 ml of 45% polyethylene glycol, MW 1540. The suspension was gently mixed for 2.5 min, after which 1 ml of DMEM was added slowly over a 30-sec period. Following a 30-sec period of mixing, 10 ml of DMEM was added slowly and allowed to incubate for 5 min at 37° C. The cell suspension was pelletized by centrifugation at 2,000 RCF for 20 min then resuspended in HAT medium to a concentration of $5 \times 10^5$ Sp 2/0 cells/ml. Fused cells were allowed to incubate at 37° C. and 6% $CO_2$ for 2 hr before plating in 96-well tissue culture plates.

Two weeks after plating, primary hybridomas were screened by indirect ELISA assay. Samples used in the first set of screening assays were plant tissue infected with CTV isolates T-36 (severe), T-4 (mild), T-26 (mild), and healthy plant tissue. Tissue was ground in liquid nitrogen, diluted 1/10 in buffer, and filtered through cheesecloth. Fifty microliters was added per well of a 96-well ELISA plate for 1 hr at 37° C. The plates were washed three times in 0.1M PBS, pH 7.4, with 0.05% Tween-20 for 5 min each. Plate wells were incubated overnight with 200 µl of PBS-1% bovine serum albumin (BSA) at 4° C., followed by washing as mentioned above. Thirty microliters of the hybridoma culture media was added per well for 1 hr at 37° C. and then washed as before. Following a 1-hr blocking step with BSA, the plates were incubated with alkaline phosphatase-labeled goat antimurine IgG and IgM for 1 hr at 37° C., then washed. Substrate solution was added for 1 hr at 37° C., after which the plates were read on an EL 309 microplate autoreader.

Screening assays showed several binding patterns of hybridomas with the different virus isolates. Among these was a hybridoma designated CTV-MCA13, which reacted with plant tissue infected with the severe CTV isolate T-36, but not with plant tissue infected with mild isolates T-4 or T-26, or with healthy plant tissue. Selected positive hybridomas were cloned twice by limiting dilution. Specific antibody was produced by injecting pristine primed mice with approximately $10^6$ cloned cells IP. The resulting ascites fluid was centrifuged for 10 min at 1,000 RCF with "Sure-Sep II" serum-plasma separators and filtered. Aliquots were either frozen or purified by affinity chromatography.

EXAMPLE 5

Isotype Determination

Antibody class and subclass were determined by indirect ELISA using reagents supplied in an isotyping kit (Zymed Laboratory, San Francisco, Calif.).

EXAMPLE 6

Purification of Immunoglobulins

Immunoglobulins were purified from ascites fluid using a Beckman rProtein A IgG purification kit (SmithKline Beckman, Fullerton, Calif.). The IgG from polyclonal antisera were purified by column chromatography on Sephacel DEAE cellulose (Pharmacia Fine Chemicals, Uppsala, Sweden)[Bar-Joseph et al., Phytopathology 69: 190-194 (1979)]. Concentrations were calculated spectrophotometrically assuming an $A_{280}$ of 1.40 for 1 mg/ml concentrations.

EXAMPLE 7

Immunoassays

Two types of indirect ELISA were used in this study. In the first, designated plate-trapped antigen (PTA), ELISA antigens were allowed to bind directly to Immulon II plates (Dynatech Labs, Alexandria, Va.) for 1 hr at 37° C. Antigens were normally prepared in 0.05M Tris buffer, pH 7.8, or in PBS. After this step and all succeeding ones, plates were washed three times with 0.1M PBS-0.05% Tween 20, pH 7.4. After incubation with the antigen preparation, plates were incubated with 1% BSA overnight at 4° C. and washed. Undiluted monoclonal antibody (MCA) growth medium, 25 to 50 μl/well, was added for screening assays, whereas 50 μl/well of 1:2000 diluted ascites fluid was added for all other assays and incubated for 1 hr at 37° C. Following a 1-hr blocking step with 1% BSA, the plates were incubated with 1:1000 diluted alkaline phosphatase-labeled goat antimurine IgG or IgM for 1 hr at 37° C. Freshly prepared substrate solution (p-nitrophenyl phosphate, Sigma Chemical Co.) was added for 1 hr at 37° C. Reactions were read on an EL 309 Microplate Autoreader (Bio-tek, Winooski, Vt.) at 405 nm.

The second indirect assay was a double antibody sandwich (DAS) ELISA where plates were coated with polyclonal antibody (1 μg/ml) for 1 hr at room temperature using conventional ELISA protocols previously described [Bar-Joseph et al., supra (1979)]. The polyclonal antisera used were antisera to unfixed, purified CTV isolates T-4 (antiserum 879) or T-36 (antiserum 1052) [Gonsalves et al., Phytopathology 68: 553-559 (1978)]. Both sera reacted specifically to CTV in conventional double-antibody sandwich ELISA tests. Antiserum 1052 reacted more strongly with its homologous antigen than with heterologous CTV isolates. The monoclonal 3DF1, previously reported reactive to all CTV strains tested [Vela et al., supra (1986, 1988)], was used as the reference antibody in DAS indirect assays. Purified IgG of 3DF1 was generously provided by C. Vela and M. Cambra.

EXAMPLE 8

Immunoelectron Microscopy

Two techniques were used to verify MCA13 binding to CTV virus. The first was a serum-specific electron microscopy (SSEM) procedure [Brlansky et al., supra] where carbon-coated 300-mesh copper grids were coated with MCA13 or purified 879 antiserum, floated on CTV-infected plant extracts, then stained with uranyl acetate. The second technique was an immunogold labeling procedure where coating of grids with 879 antiserum and floating on CTV-infected extracts were the same as in SSEM. The grids then were washed by floating on drops of PBS three times for 5 min, followed by floating for 3 hr on diluted 1:1000 CTV-MCA13 ascites. Grids were washed as above and floated on 20 nm gold-labeled goat antimouse IgG (E-Y Laboratories, San Mateo, Calif.) for 2 hr. Washing was repeated and grids were stained with uranyl acetate as in the SSEM procedure. Immunogold labeled control grids were processed as above, except that the CTV-MCA13 coating step was eliminated. The grids were examined by a Phillips 201 transmission-electron microscope for CTV detection and gold labeling.

EXAMPLE 9

Field Test

Samples of citrus were collected from a grove near Clewiston, Fla. The sample set contained stem tissue from trees infected with severe CTV and mild CTV, as well as from trees from areas where poor growth was due to horticultural problems.

Blind assay of the samples using monoclonal antibody from CTV-MCA13, ATCC No. HB10140, in an enzyme-linked immunosorbent assay correctly identified severe isolates of CTV with greater than 90% accuracy.

It is understood that the foregoing detailed description is given mainly by way of illustration and that modifications and variations may be made therein without departing from the spirit and scope of the invention.

We claim:

1. A hybridoma cell line, wherein the cells thereof are capable of producing and secreting into a growth medium therefor a monoclonal antibody which binds selectively with severe citrus tristeza virus.

2. A cell line as described in claim 1, wherein said cell line is ATCC No. HB-10140.

3. A monoclonal antibody produced by the cell line of claim 1.

4. A monoclonal antibody produced by the cell line of claim 2.

5. A method of detecting infections of severe citrus tristeza virus in citrus comprising:
   a) selecting tissue from citrus plants:
   b) subjecting said tissue to an immunosorbent assay using a monoclonal antibody capable of selectively binding with severe citrus tristeza virus.

6. The method of claim 5 wherein said monoclonal antibody is produced by the cell line ATTC No. HB-10140.

7. A kit for detecting infections of severe citrus tristeza virus in citrus comprising a solid substrate having bound thereto a monoclonal antibody capable of selectively binding with said severe citrus tristeza virus.

8. A kit as described in claim 7 wherein said monoclonal antibody is produced by the cell line ATTC No. HB-10140.

9. A kit as described in claim 7 wherein the substate is a microtiter plate.

10. A kit as described in claim 7 and further comprising a detectable-labeled antibody capable of binding with said virus.

* * * * *

UNITED STATES PATENT AND TRADEMARK OFFICE
CERTIFICATE OF CORRECTION

PATENT NO. : 5,104,789
DATED : April 14, 1992
INVENTOR(S) : Thomas A. Permar and Stephen M. Garnsey It is certified that error appears in the above-identified patent and that said Letters Patent is hereby corrected as shown below:

On the Title page, item [57]

In the Abstract, line 5, delete "isolaates" and insert -- isolates -- .
Column 3, line 46, delete "Nibleck" and insert -- Niblett -- .
Column 4, line 11, delete "pristine" and insert -- pristane -- .
Column 7, line 23, delete "5 to the 12" and insert -- 5 of the 12 -- .
Column 11, line 6, delete "pristine" and insert -- pristane -- .

Signed and Sealed this

Twenty-eighth Day of September, 1993

Attest:

BRUCE LEHMAN

*Attesting Officer*   *Commissioner of Patents and Trademarks*